(12) United States Patent
Liu et al.

(10) Patent No.: US 11,344,906 B2
(45) Date of Patent: May 31, 2022

(54) NEEDLE-TYPE VIBRATE-TO-NEBULIZE APPARATUS AND NEBULIZER

(71) Applicant: Shenzhen Loxim Technologies Co.,Ltd, Shenzhen (CN)

(72) Inventors: Biaoqi Liu, Shenzhen (CN); Yunfang Zheng, Shenzhen (CN)

(73) Assignee: Shenzhen Loxim Technologies Co., Ltd, Shenzhen (CN)

( * ) Notice: Subject to any disclaimer, the term of this patent is extended or adjusted under 35 U.S.C. 154(b) by 0 days.

(21) Appl. No.: 17/002,917

(22) Filed: Aug. 26, 2020

(65) Prior Publication Data

US 2021/0053086 A1 Feb. 25, 2021

Related U.S. Application Data

(63) Continuation of application No. PCT/CN2019/101976, filed on Aug. 22, 2019.

(51) Int. Cl.
*B05B 17/06* (2006.01)

(52) U.S. Cl.
CPC ...... *B05B 17/0653* (2013.01); *B05B 17/0676* (2013.01)

(58) Field of Classification Search
CPC ............ B05B 17/0653; B05B 17/0676; B05B 7/0012; B05B 17/063; A61L 2209/11; A61L 9/122; A61L 2209/132; A61L 9/14
See application file for complete search history.

(56) References Cited

U.S. PATENT DOCUMENTS

| | | | | |
|---|---|---|---|---|
| 7,168,636 B2 * | 1/2007 | Lebeda | .................. | A01F 25/00 239/389 |
| 2013/0206857 A1 * | 8/2013 | Ivri | .................... | B05B 17/0669 239/4 |

(Continued)

FOREIGN PATENT DOCUMENTS

| | | |
|---|---|---|
| CN | 1304927 A | 7/2001 |
| CN | 201469727 U | 5/2010 |

(Continued)

OTHER PUBLICATIONS

International Search Report of PCT/CN2019/101976, dated May 18, 2020.

*Primary Examiner* — Qingzhang Zhou
*Assistant Examiner* — Joel Zhou
(74) *Attorney, Agent, or Firm* — W&KIP

(57) ABSTRACT

Disclosed is a needle-type vibrate-to-nebulize apparatus and nebulizer for nebulizing fluids, in particular essential oils. The needle-type vibrate-to-nebulize apparatus mainly comprises the air passage designed in the module, the steel needle and the vibrating unit. Fluid is delivered from the rear end to the front end, then nebulized at the front end by high-frequency vibration. The nebulized mist is blown out through the air passage. The nebulizer mainly comprises the needle-type vibrate-to-nebulize apparatus and the peristaltic pump with rollers. The peristaltic pump with rollers is capable of sucking and supplying essential oil to the steel needle, as well as reversing the oil back when power off to prevent clogging. High-frequency vibrating action of the vibrating unit is generated by the piezoelectric disk and induced to the steel needle. As a result of resonation, essential oil is nebulized at the front end and blown out through the air passage.

8 Claims, 11 Drawing Sheets

(56) References Cited

U.S. PATENT DOCUMENTS

2017/0298407 A1* 10/2017 Demokritou .......... A23L 3/3463
2018/0326112 A1    11/2018 Mushtaq et al.
2021/0100963 A1*  4/2021 McDonnell .............. B06B 1/06

FOREIGN PATENT DOCUMENTS

| CN | 202113372 U | 1/2012 |
|---|---|---|
| CN | 102500502 A | 6/2012 |
| CN | 203916959 U | 11/2014 |
| CN | 203970976 U | 12/2014 |
| CN | 204072868 U | 1/2015 |
| JP | 2765747 B2 | 6/1998 |

* cited by examiner

NEEDLE-TYPE VIBRATE-TO-NEBULIZE APPARATUS AND NEBULIZER

CROSS REFERENCE TO RELATED APPLICATION

This application is a continuation of international application PCT/CN2019/101976, filed on Aug. 22, 2019, the entire disclosure of which is incorporated herein by reference in its entirety.

TECHNICAL FIELD

The object of the application is a needle-type vibrate-to-nebulize apparatus and nebulizer suited for directly nebulizing essential oils into tiny particles and diffusing out. The application is related to the aroma diffusing device.

BACKGROUND

Two types of aroma diffusing device are known: ultrasonic diffuser (with water) and waterless diffuser. The ultrasonic diffuser is using ultrasonic sound, aka high-frequency vibration generated by a piezoelectric transducer at the bottom of a water reservoir, to disperse water mist by overcoming the surface tension. Essential oil is dropped into the water and diffused out together with water mist. The application using ultrasonic technology is mature and popular in the market. However, it is not convenient for clean and maintenance of reservoir. And it is impossible to achieve precise consumption for those water-insoluble essential oils. Therefore, more and more consumers prefer waterless diffuser.

Waterless diffuser is capable of diffusing essential oil directly without water. Currently there are two common direct diffusing devices in the market. The first one uses Venturi effect. With the help of compressed air generating vacuum at jet nozzle, the essential oil is sucked out by vacuum and then atomized at the outlet of the nozzle. When the atomized mist is blown out to the ambience, essential oil droplets flow back to the oil bottle through a spiral channel. The present Venturi atomizer has two disadvantages. First, it is so noisy with the jet nozzle design that not suited for quiet environments. And also, the atomizing consumption for different essential oils varies and the differences could go up to tens of times. The other one uses piezoelectric vibrating plate, on which several tens to hundreds of minute holes are fabricated. Essential oil is nebulized when the plate vibrates at resonant frequency. There are two drawbacks from the technology. First, the minute holes, recommended for spray water mist only, are easy to clog for viscous oils. Secondly, oil flows by its gravity therefore the nebulizing consumption of essential oil is not adjustable.

In view of above, there is an improvement opportunity for direct diffusing devices.

SUMMARY OF THE APPLICATION

In order to address at least one of the above technical problems, the purpose of the present application is to design a novel needle-type vibrate-to-nebulize apparatus and nebulizer to directly nebulize essential oil.

The specific solution in the present application as below:

Firstly, design a needle-type vibrate-to-nebulize apparatus comprising:

A module. There is an air passage designed in the module.

A module cap. The module cap is assembled at the top of the module.

A steel needle. The steel needle is a hollow conduit. Both front and rear ends of the steel needle are coupled with seal units. The front end is seated into the air passage. And the rear end is for receiving fluid.

A vibrating unit. The vibrating unit is assembled with the module. And it contains a piezoelectric disk and a steel plate.

The piezoelectric disk is attached to the steel plate coupled with the steel needle. When the piezoelectric disk is excited, the vibrating action is induced from the steel plate to the steel needle. The resonant vibration at the front end of the needle provides sufficient energy to nebulize fluid.

Wherein the design of air passage contains chamber, board, connect-in space and mist blow-off channel. There is an air outlet designed in the chamber and the board separates the chamber from the connect-in space. There is an open at the top of the board to connect the chamber and the connect-in space. And there is a passageway with blocker between the connect-in space and mist blow-off channel.

Wherein the connect-in space and mist blow-off channel are designed parallelly.

According to the application, the needle-type vibrate-to-nebulize apparatus comprises a fan. The fan is mounted on the module. With the intake from the direction of the steel plate, the fan blows the air into the inlet of the chamber.

According to the application, the needle-type vibrate-to-nebulize apparatus further comprises a socket. The rear end of the steel needle is held by the socket which is mounted to the module.

Secondly, the application also includes a nebulizer comprising:

The needle-type vibrate-to-nebulize apparatus mentioned above.

A peristaltic pump with rollers for supplying fluid to the needle-type vibrate-to-nebulize apparatus.

Wherein the peristaltic pump with rollers contains an elastic tube connected with the steel needle.

According to the application, the nebulizer comprises:

A bottle, with essential oil, screwed with the module.

The peristaltic pump with rollers contains a tube immersed into the bottle for sucking and supplying fluid to the steel needle.

According to the application, the nebulizer also comprises:

A control board connecting to control the peristaltic pump with rollers and the needle-type vibrate-to-nebulize apparatus.

Wherein the control board contains a PCB board with micro control units, plug-in interfaces and operating buttons. The PCB board controls the peristaltic pump with rollers and the needle-type vibrate-to-nebulize apparatus.

The needle-type vibrate-to-nebulize apparatus in the present application mainly comprises the air passage designed in the module, the steel needle and the vibrating unit. Fluid is delivered from the rear end to the front end, then it is nebulized at the front end by high-frequency vibration. The nebulized mist is blown out through the air passage. The apparatus has improved compatibility for most types of fluids with various range of viscosity.

The nebulizer in the present application mainly comprises the needle-type vibrate-to-nebulize apparatus and the peristaltic pump with rollers. The peristaltic pump with rollers is capable of essential oil sucking and supplying to the steel needle, as well as reversing the oil back when power off to prevent clogging. High-frequency vibrating action of the vibrating unit is generated by the piezoelectric disk and induced to the needle. As a result of resonation at the front end, essential oil is nebulized and blown out through the air passage. The device in the present application is capable of precisely controlling the consumption of essential oil. With compact size, maintenance free and low-noise performance, the device is suited for quiet environments such as bedrooms and hospitals. User experiences of aromatherapy are well improved.

BRIEF DESCRIPTION OF THE DRAWINGS

In order to clearly illustrate the technical solutions in the embodiments of the present application, the FIGs used in the illustration of the embodiments will be briefly described below. Obviously, the FIGs in the following description are merely some embodiments of the present application. Those who skilled in this field can obtain other FIGs according to the structures shown in these FIGs without any creative work.

The design, features and advantages of the present application will be further illustrated with references of the embodiments.

DESCRIPTION OF THE EMBODIMENTS

According to the FIGs, the technical solutions in the embodiments of the present application will be described clearly and completely as below. Apparently, the described embodiments are just parts of embodiments, but not all of the embodiments of the present application. Those who skilled in this field obtaining the other embodiments based on the embodiments of the present application without creative efforts shall be within the protection scope of the present application.

It should be noted that the description of "first", "second", and the similar words in the present application are only used for the purpose of description. They cannot be understood as indicating or implying its relative importance or implicitly indicating the numbers of indicated technical features. Thus, features defined as "first", "second" may explicitly or implicitly include at least one such feature. In addition, the technical solutions between various embodiments can be combined with each other, but they must be based on the design from those who skilled in this field. When the combination of technical solutions is contradictory or unachievable, it should be considered that the combination of the technical solutions does not exist. And it is not within the scope of protection claimed by the present application.

The needle-type vibrate-to-nebulize apparatus and nebulizer in the present application is illustrated in FIG. 1-FIG. 11.

Refer to FIG. 5-FIG. 9. The needle-type vibrate-to-nebulize apparatus 20 comprises:

The module 21 being the base of assembling. There is an air passage designed in the module for blowing out the nebulized essential oil mist.

The module cap 24 assembled at the top of the module 21 to form the air passage.

The steel needle 224 being a hollow conduit. Both front end 224A and rear end 224B of the steel needle 224 are coupled with seal units. The front end 224A is seated into the air passage. And the rear end 224B is for receiving fluid. Specifically, the front end 224A, coupled with the sealing part 226, is seated into air passage. And the rear end 224B coupled with seal tube 227 is for receiving fluid.

Figure 7:
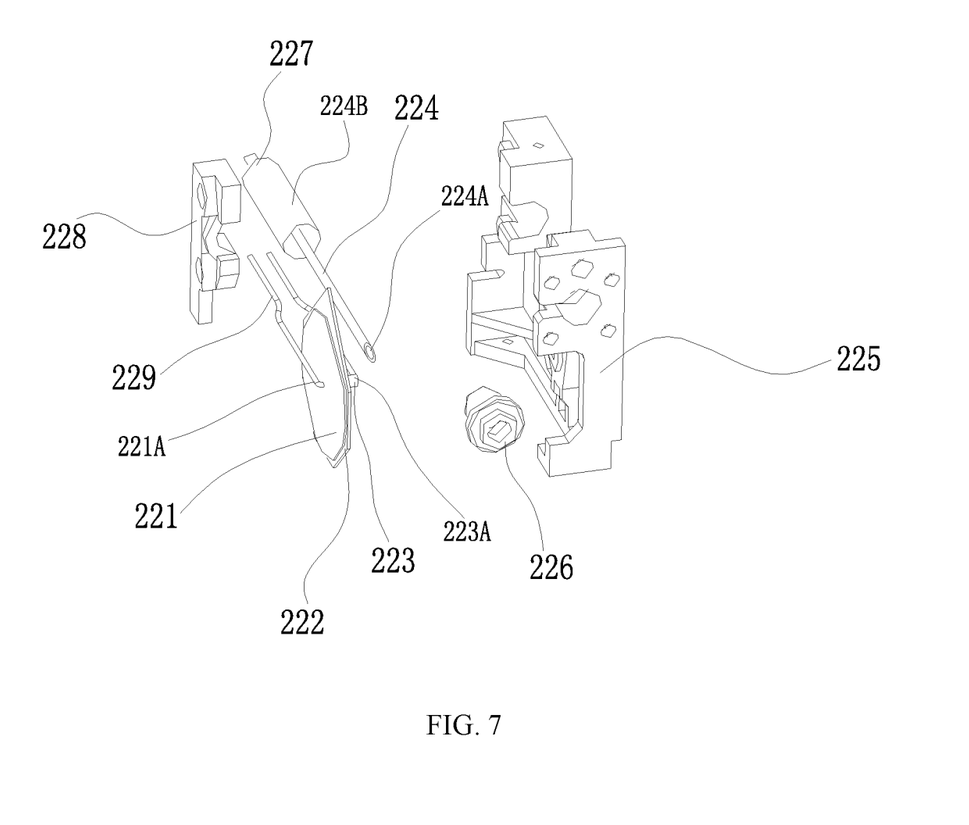
FIG. 7 is the explosive view of the vibrating unit 22 in FIG. 6 according to the application.

The vibrating unit 22. The vibrating unit 22 contains the piezoelectric disk 221, the steel plate 222, the steel column 223, the frame 225 and the misting wire 229. The piezoelectric disk 221 and the steel plate 222 are attached together by conductive adhesive. The steel column 223 is laser-welded to the steel plate 222. Then the whole unit is mounted to the frame 225. One electrode of misting wire 229 is soldered to the center 221A of the piezoelectric disk 221. The other electrode is soldered to the steel column end 223A. The piezoelectric disk 221 transfers electricity to high-frequency vibration.

It can be understood that when the piezoelectric disk 221 is excited, the vibrating action is induced through the steel plate 222 to the steel needle 224. The resonant vibration at the front end 224A of the needle provides sufficient energy to nebulize fluid. And the nebulized mist is blown out through the air passage.

Figure 6:
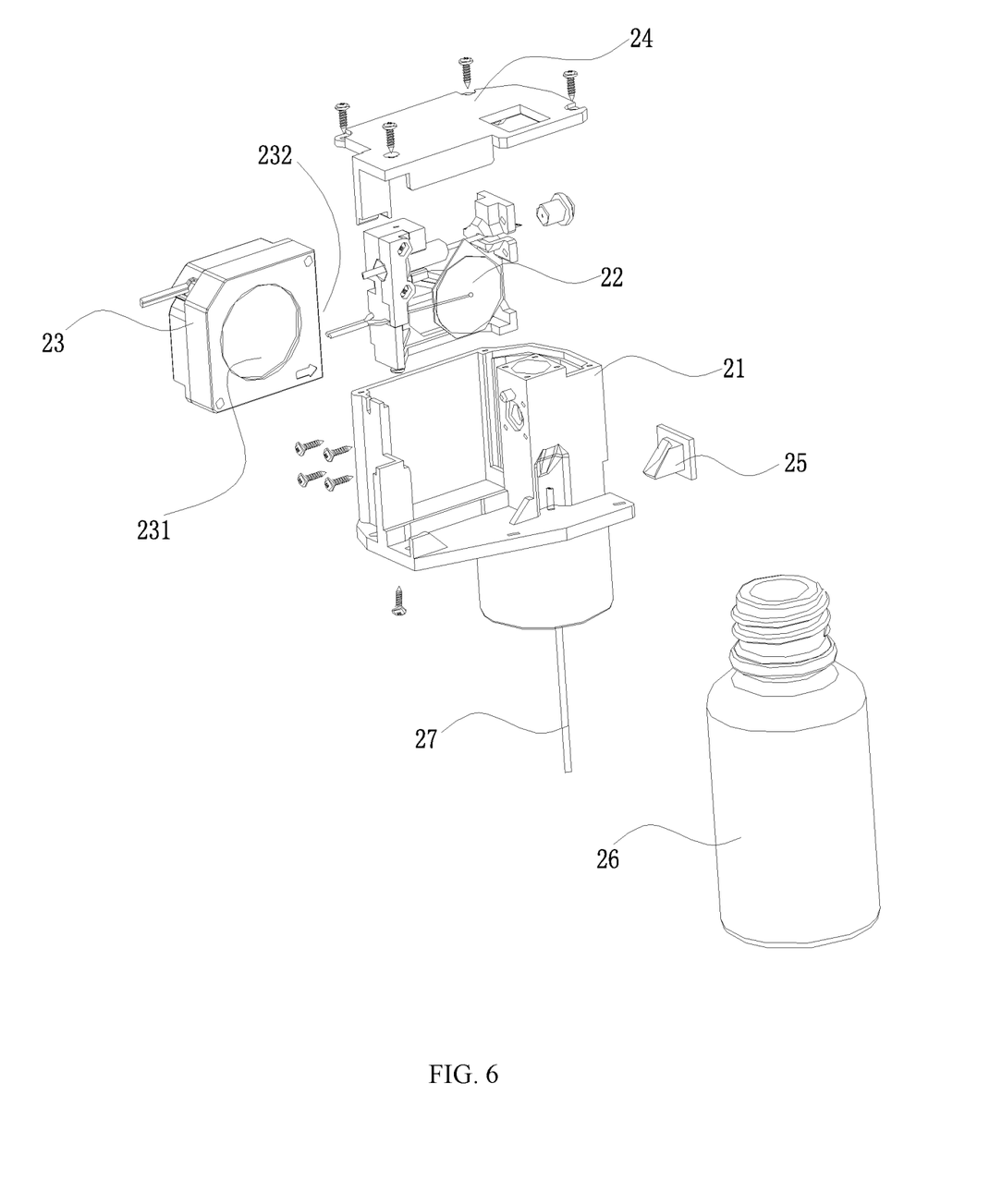
FIG. 6 is the explosive view of the needle-type vibrate-to-nebulize apparatus 20 in FIG. 5 according to the application.

The needle-type vibrate-to-nebulize apparatus comprises the socket 228 to enable the resonation of the front end 224A. The rear end 224B of the steel needle 224 is held by the socket 228 which is mounted to the module 21.

Figure 8:
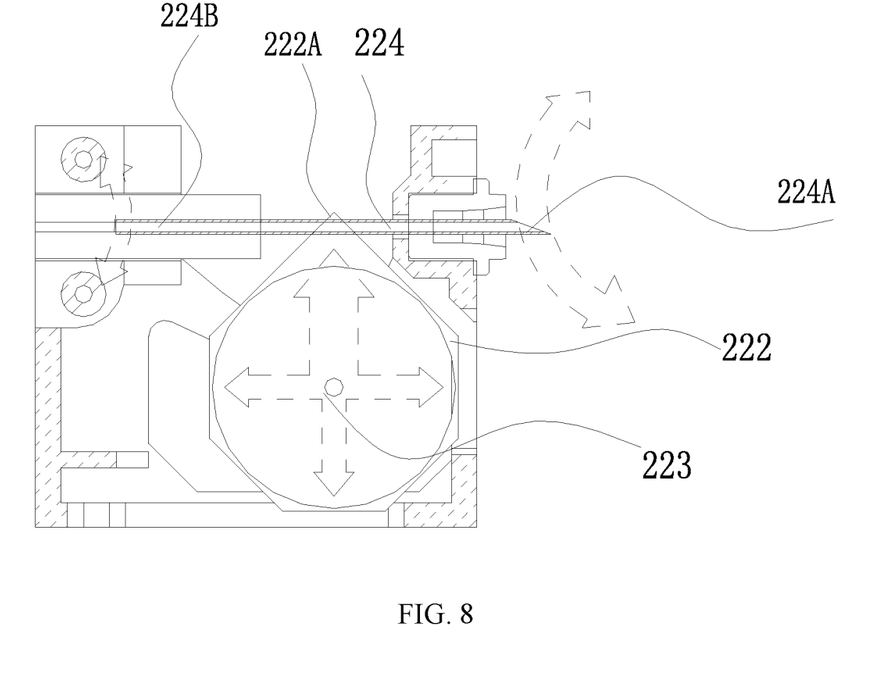
FIG. 8 illustrates the vibrating mode of the piezoelectric disk 221 and the front end 224A of the steel needle according to the application.

Refer to FIG. 8. FIG. 8 illustrates the vibrating mode of the piezoelectric disk 221 and the front end 224A of the steel needle. Through the misting wire 229, high-frequency signal drives the piezoelectric disk 221 vibrating accordingly, which is high-frequency and radial. The vibrating action is shown as arrow direction in the FIG. 8. The steel column 223 is at the center as an idle point. The steel plate 222 is not symmetric with a junction 222A soldered to the steel needle 224. The junction 222A by design has the biggest radial amplitude. The vibration energy, transferred from steel plate 222, is induced to the steel needle 224. If the dimension is well calculated, the maximum vibrational amplitude occurs at the front end 224A and rear end 224B, as shown in the FIG. 8. As the seal tube 227 held by the socket 228, the resistance at rear end 224B is higher than that at the front end 224A coupled with sealing part 226. Therefore, the vibration at front end 224A is amplified further. Above all, the vibrational amplitude reaches maximum at the front end 224A. The mechanical energy generated by the vibrating piezoelectric disk 221 is concentrated at front end 224A and nebulizes fluid into mist.

Figure 9:
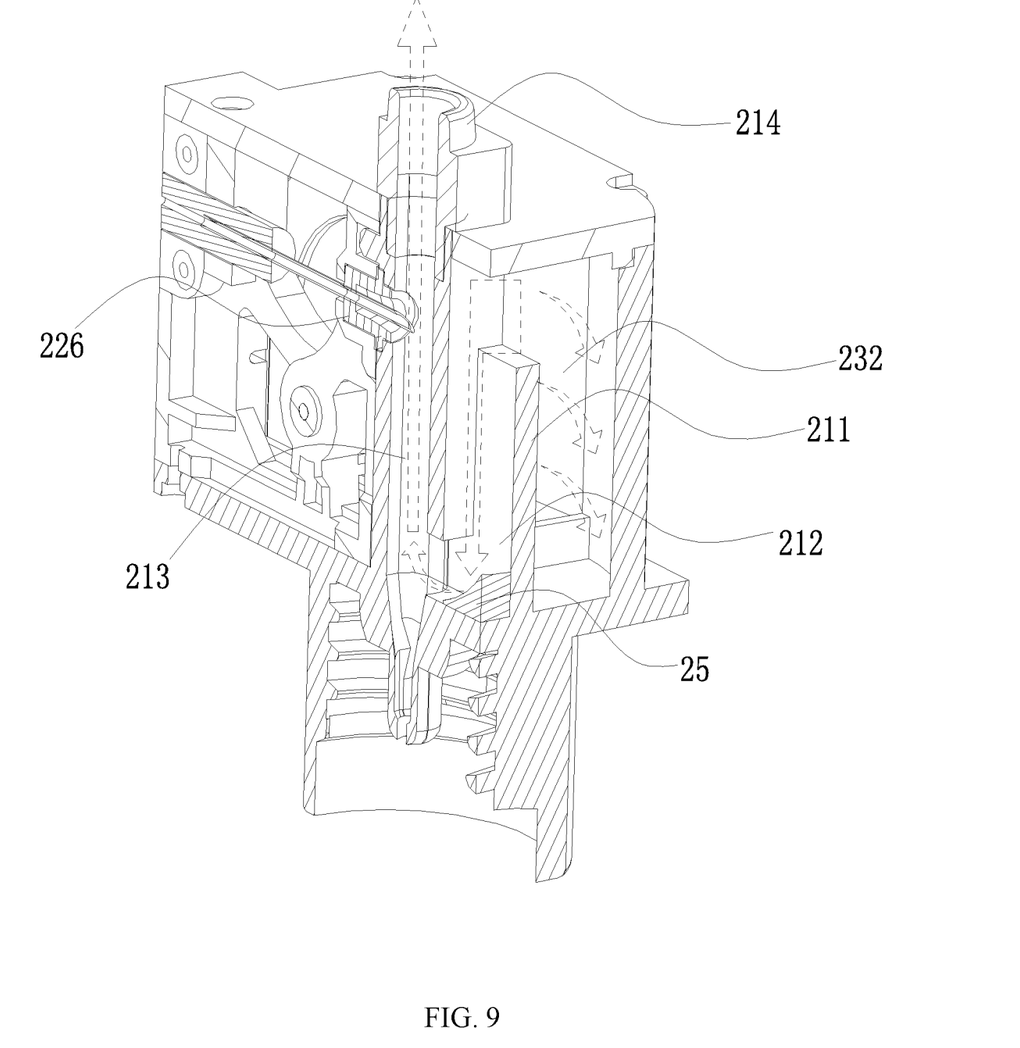
FIG. 9 is the view of the air passage in the module 21 according to the application.

In the most preferred embodiment, the air passage contains chamber, board 221, connect-in space 212 and mist blow-off channel 213. There is an air outlet designed in the chamber and the board 211 separates the chamber from the connect-in space 212. There is an open at the top of the board 211 to connect the chamber and connect-in space 212. And there is a passageway with blocker 25 designed between the connect-in space 212 and mist blow-off channel 213. The blocker sticks to the passageway by glue. With the design above, the air passage is formed.

Wherein the mist blow-off channel 213 and the connect-in space 212 are built in "U" shape. The seal ring 214 is coupled to outlet of the mist blow-off channel 213 to prevent fluid leaking out to other units in the apparatus.

The needle-type vibrate-to-nebulize apparatus comprises the fan 23. The fan is mounted on the module 21. With the intake 231 from the direction of the steel plate 222, the fan 23 blows the air into the inlet of the chamber via outtake 232.

A centrifugal fan 23 is used in the present application. The intake 231 is positioned toward the steel plate 222 to cool down the vibrating unit 22. The outtake 232 is connected with the inlet of the chamber. Through the air passage, the nebulized mist is blown out to ambience by air flow from the fan 23. Further, the module cap 24 is designed to form the air passage, while helps the assembling of the fan 23.

Refer to FIG. 9. FIG. 9 is the view of the air passage in the module 21. Through the outtake 232, the fan blows the air to the chamber between the module 21 and module cap 24. The air flow runs up across the board 211, and down through the connect-in space 212. Passing by the blocker 25, the air flow finally goes up straight to the mist blow-off channel 213. The front end 224A, coupled with the sealing part 226, crosses into the mist blow-off channel 213. The essential oil is nebulized at the front end 224A and the mist is blown out to ambience via the mist outlet coupled with seal ring 214. Giving the shape design of the air passage together with sealing part 226 and seal ring 214, the nebulized mist is isolated from the working system therefore no contamination occurred. It is suggested to use centrifugal fan for the fan 23 design, considering the losses of air flow energy along the air passage.

Figure 1:
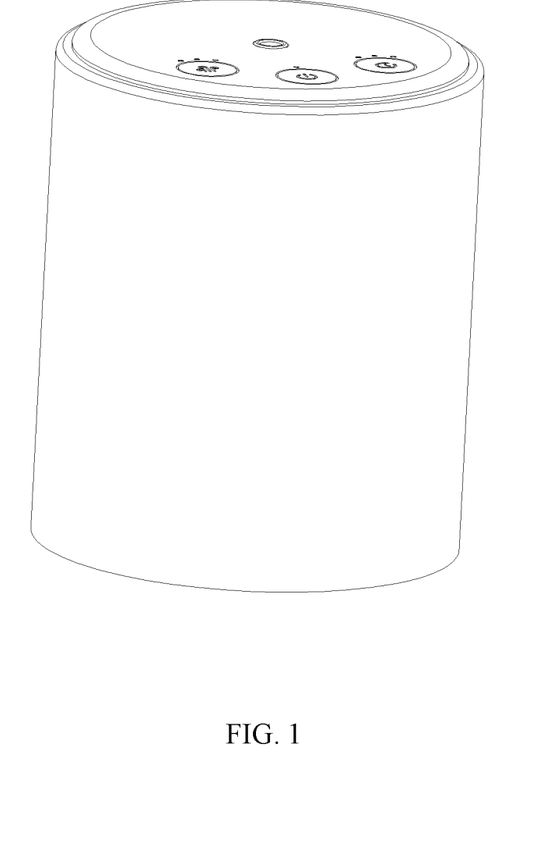
FIG. 1 is the sketch view of the nebulizer for directly nebulizing essential oil according to the application.
Figure 2:
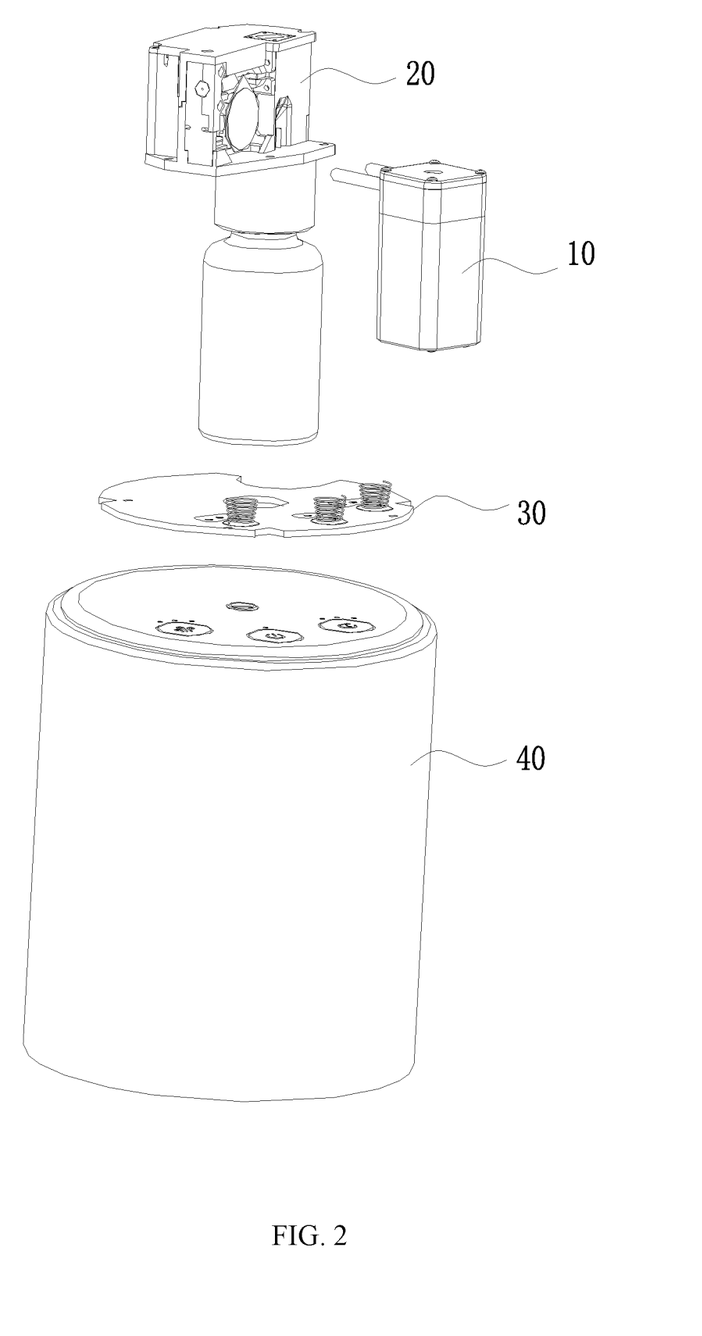
FIG. 2 is the explosive view of the nebulizer in FIG. 1 according to the application.

Refer to FIG. 1-FIG. 11. FIG. 1 is the sketch view of the nebulizer for directly nebulizing essential oil in the present application. FIG. 2 is the explosive view of the nebulizer in FIG. 1. The nebulizer comprises:

The needle-type vibrate-to-nebulize apparatus 20 containing the vibrating unit 22 and the steel needle 224. By the resonant vibration induced from the vibrating unit to the steel needle 224, the fluid is nebulized at the front end 224A and blown out to the ambience by the fan 23.

The peristaltic pump with rollers 10 for sucking and supplying fluids, for example essential oil, to the needle-type vibrate-to-nebulize apparatus 20 in precise dosage.

In the most preferred embodiment, the peristaltic pump with rollers 10 contains the elastic tube 15 connected to the steel needle 224.

Specifically, the tube outlet 151 is connected with the seal tube 227 at the rear end. The essential oil is sucked by the peristaltic pump with rollers 20 and delivered to front end 224A via the steel needle 224.

The nebulizer comprises the bottle 26. The bottle with fluid is screwed to the module 21. And it contains the tube 27 immersed in the bottle. The fluid in the bottle is sucked and supplied by the peristaltic pump with rollers 10 to the steel needle 224 via the tube 27.

In the present embodiment, the bottle 26 is to store the oil. The tube 27 connected to the tube inlet 152 is for oil supply.

In the other embodiments, the fluids can be essential oils, fragrances or other treatment liquids.

In the present embodiment, essential oil is directly nebulized by the combination of the peristaltic pump with rollers 10 and needle-type vibrate-to-nebulize apparatus 20. In a detailed illustration, the nebulizer further comprises the control board 30 for operating control and the nebulizer body 40.

Figure 10:
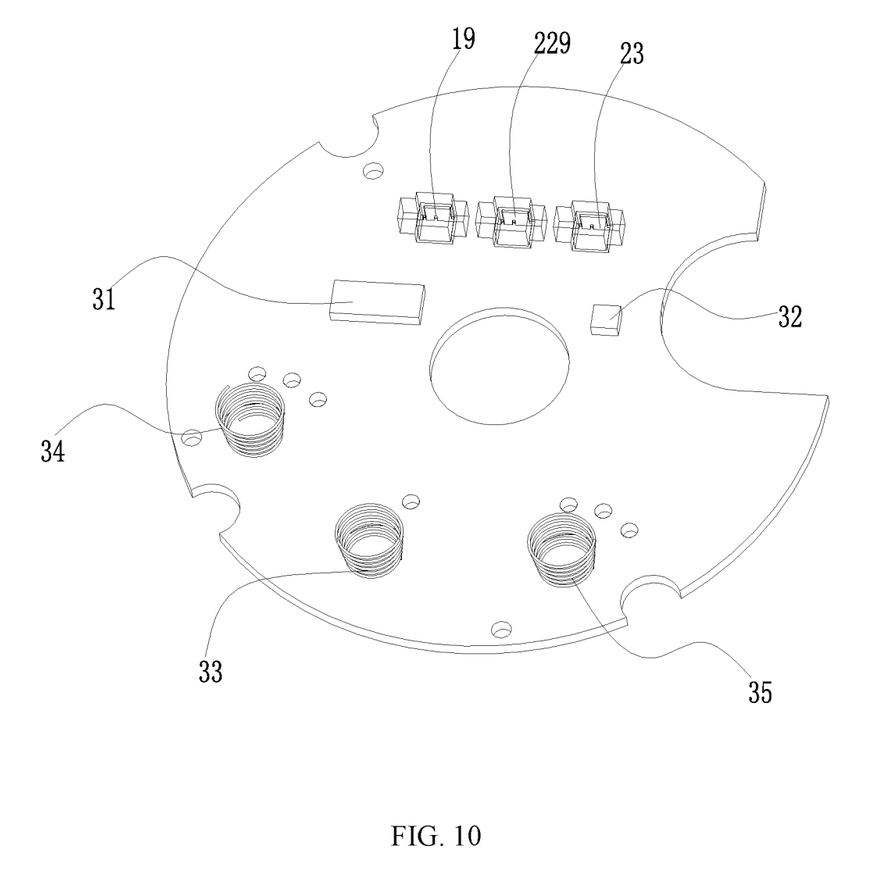
FIG. 10 is the view of the control board 30 according to the application.

The control board 30 is connected to control the peristaltic pump with rollers 10 and the needle-type vibrate-to-nebulize apparatus 20.

The control board is to control the peristaltic pump with rollers 10, the piezoelectric disk 221 in the needle-type vibrate-to-nebulize apparatus 20 and the fan 23. It also controls the power on/off, the timer and the misting mode.

Specifically, the control board 30 contains a PCB board with micro control units 31, plug-in interfaces and operating buttons. The PCB board controls the peristaltic pump with rollers 10 and the needle-type vibrate-to-nebulize apparatus 20.

Figure 11:
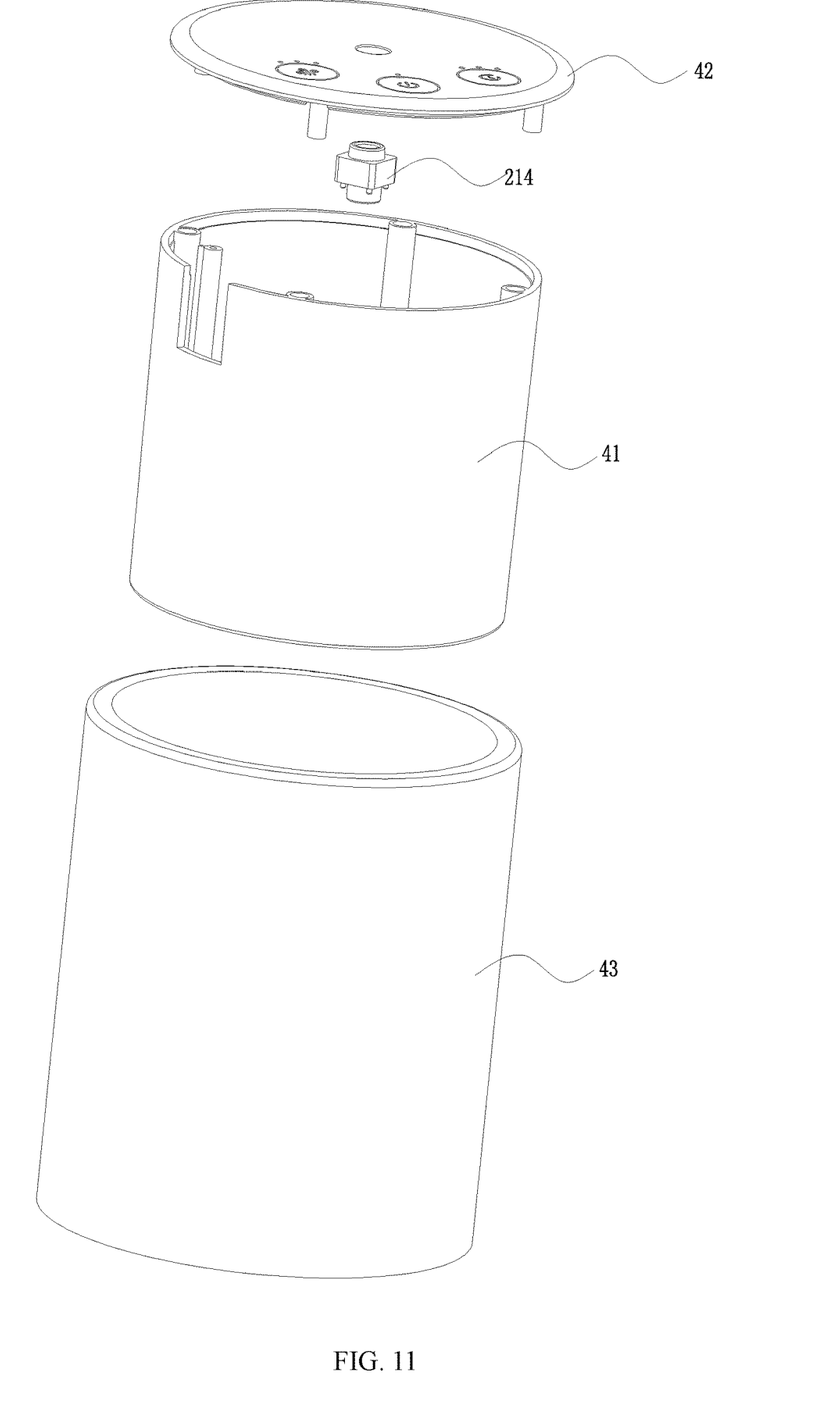
FIG. 11 is the view of the nebulizer body 40 according to the application.

The nebulizer body 40 contains top panel 42, interior and exterior parts.

In the present embodiment, the peristaltic pump with rollers 10 is for essential oil sucking and supplying to the needle-type vibrate-to-nebulize apparatus 20 in precise dosage, as well as reversing the oil when power off. In the vibrating unit 22, the high-frequency vibrating of the piezoelectric disk 221 is induced to the steel needle 224. As the result of resonation, the vibrational amplitude of the front end 224A reaches maximum to nebulize essential oil. Finally, the nebulized mist is blown out to ambience by the fan 23. The peristaltic pump with rollers 10, the vibrating unit 22 of the needle-type vibrate-to-nebulize apparatus 20 and the fan 23 work with low noise. The overall noise level of the nebulizer is lower than 35 dB so that it is suited for quiet environments such as bedrooms and hospitals. Further with seal units, the nebulizer has an isolation design for the peristaltic pump with rollers 10 and the needle-type vibrate-to-nebulize apparatus 20. It is easy to operate with minimum maintenance efforts. Meanwhile, the software setting of the control board 30 precisely determines the consumption of essential oil as well as the timer of the nebulizer.

Figure 3:
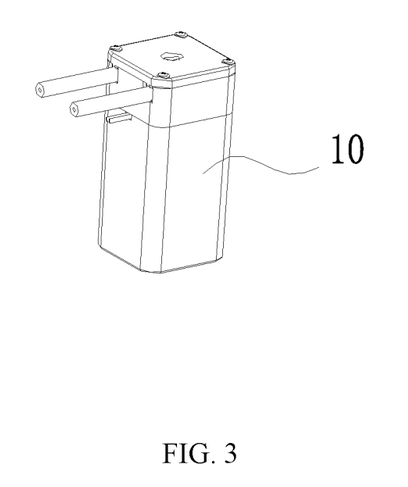
FIG. 3 is the schematic view of the peristaltic pump with rollers 10 in FIG. 2 according to the application.
Figure 4:
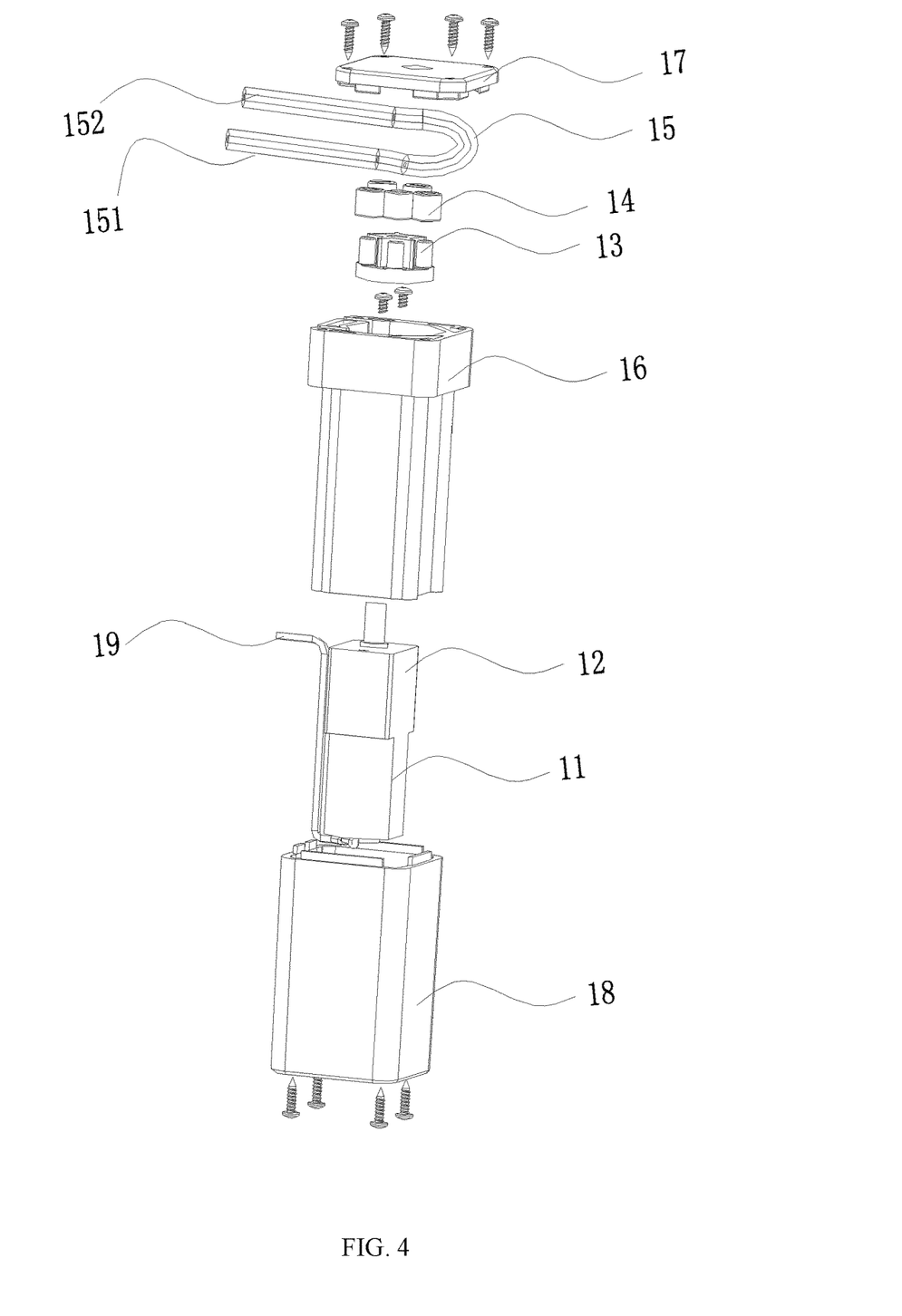
FIG. 4 is the explosive view of the peristaltic pump with rollers 10 in FIG. 3 according to the application.
Figure 5:
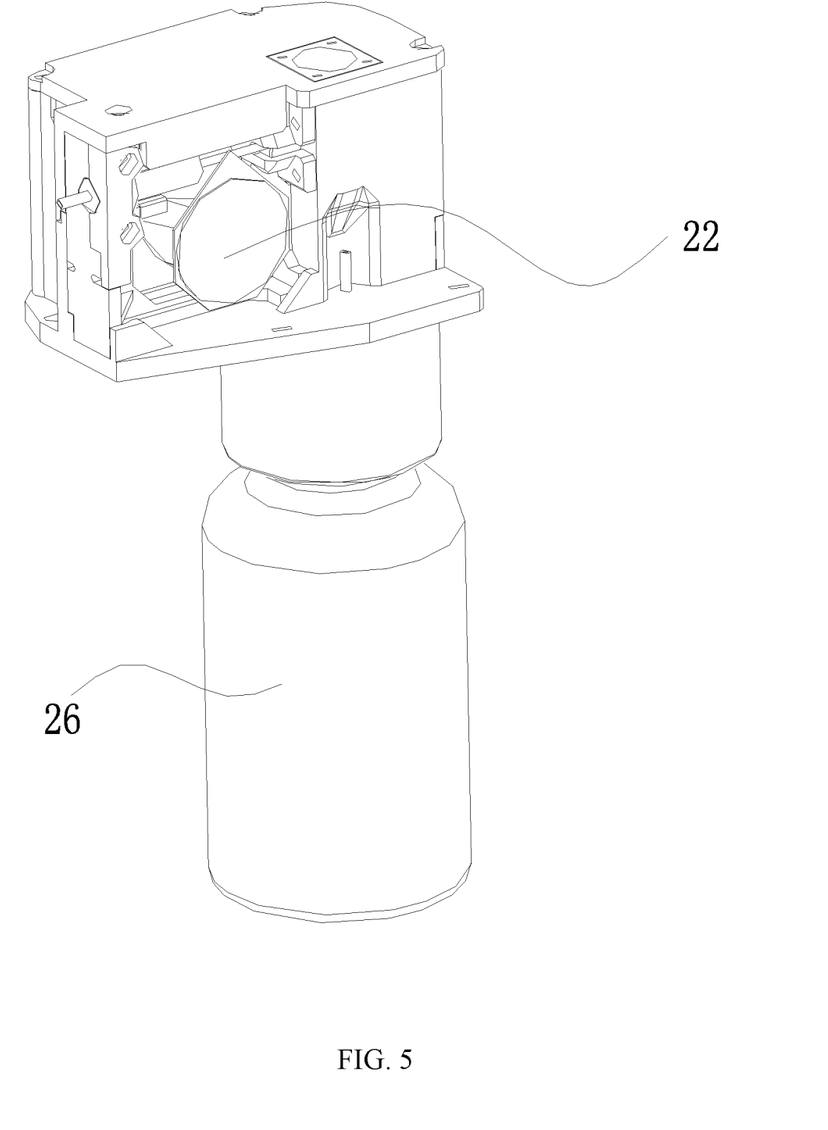
FIG. 5 is the schematic view of the needle-type vibrate-to-nebulize apparatus 20 according to the application.

Refer to FIG. 2 to FIG. 4. FIG. 3 is the schematic view of the peristaltic pump with rollers 10 in FIG. 2. FIG. 4 is the explosive view of the peristaltic pump with rollers 10 in FIG. 3. Specifically, the peristaltic pump with rollers 10 contains the motor 11, the gear box 12, the rotor 13, the rollers 14, the elastic tube 15, the pump body 16, the pump cap 17, the cover 18 and the motor wire 19. Through the gear box 12, the running speed of the motor 11 is reduced from 10000 RPM to 10-30 RPM. The rotor 13 rotates at the reduced speed from the gear box 12. The rollers 14 are seated in and rotate together with the rotor 13. The compressing of the rollers 14 to the elastic tube 15 moves the essential oil toward the tube outlet 151. Simultaneously, the bouncing-back of the elastic tube 15 generates vacuum to suck out essential oil from the tube inlet 152. The continuous rotating of the rollers 14 driven by the rotor 13 creates continuous fluid sucking out from the tube inlet 152 to the tube outlet 151. The pump body 16, pump cap 17 and the cover 18 are to hold and mount the remaining parts. And the motor wire 19 is for connecting the electrodes of the motor 11 to the control board 30.

The rotating of the rollers 14 helps reducing friction with the elastic tube 15, therefore extends the life time of the elastic tube 15. The number of the rollers 14 is suggested at odd number. In the present embodiment, the number is five and other choices in odd number (for example, three, seven, nine or etc.) are also feasible. It is understandable the higher number of the rollers 14 means higher complexity of mechanical design, while the less number may cause pulsation of oil delivery from the peristaltic pump with rollers 10.

Reverse signal is sent to the motor 11 by the control board 30, for controlling the peristaltic pump with rollers 10 reversing essential oil from the tube outlet 151 to the tube inlet 152. The voltage of the motor is adjustable from the control board 30, therefore the rotating speed of the peristaltic pump with rollers 10 is controlled accordingly. As a result, the consumption of essential oil is controllable.

Refer to FIG. 10. FIG. 10 is the view of the control board 30. High-frequency signal generated by the micro control units 31 is amplified by the power amplifier 32. Via the motor wire 229, the amplified signal is sent to drive the piezoelectric disk 221 exciting. With the induced vibrating of the vibrating unit 22, the resonation occurs with maximum amplitude at the front end 224A where the essential oil is nebulized. The micro control units 31 are connected to the motor 11 by motor wire 19 and control the peristaltic pump with rollers 10 to suck out essential oil from the bottle and supply to the front end 224A. The fluid consumption for the peristaltic pump with rollers 10 is precisely controlled by adjusting the voltage of the motor 11. Reverse signal is sent to the motor 11 by the micro control units 31 in case of power off, to control the peristaltic pump with rollers 10 reversing essential oil from the vibrating unit 20. Then there is no clogging at the front end 224A. The micro control units 31 controls the fan 23 and three touch buttons: power 33, timer 34 and misting mode 35. The control board 30 also contains power supply and other necessary electric circuits.

Refer to FIG. 11. FIG. 11 is the view of the nebulizer body 40. The nebulizer body 40 contains the interior 41, the top panel 42 and the exterior 43. In the present application, it provides one of the examples of the nebulizer body design. Wherein the touch buttons at the top panel 42 are linked to the control buttons 33, 34 and 35 on the control board 30. The top panel 42 is well coupled with the seal ring 214. The nebulizer body 40 can be designed and decorated as needed.

The above description is only a preferred embodiment of the present application, and thus does not limit the scope of patents of the present application. According to the inventive concept of the present application, equivalent structural transformations made using the contents of the present specification and drawings, or directly or indirectly applied in other related technical fields, are all included in the scope of protection of the present application.

We claim:

1. A nebulizer, comprising:
a needle nebulizer;
wherein, the needle nebulizer comprising:
a module, wherein the module comprises an air passage;
a module cap, wherein the module cap is assembled at the top of the module;
a steel needle, wherein the steel needle is a hollow conduit, both front and rear ends of the steel needle are coupled with seal units, the front end is seated into the air passage, and the rear end is for receiving fluid; and
a vibrating unit, wherein the vibrating unit is assembled with the module, and the vibrating unit contains a piezoelectric disk and a steel plate;
wherein the piezoelectric disk is attached to the steel plate coupled with the steel needle; when the piezoelectric disk is excited, a vibrating action is induced from the steel plate to the steel needle; a resonant vibration at the front end of the needle provides energy to nebulize fluid;
a peristaltic pump with rollers for supplying fluid to the needle nebulizer;
the air passage of the module comprises a chamber, a board, a connect-in space and a mist blow-off channel;
the chamber comprises an air outlet designed in the chamber, and the board separates the chamber from the connect-in space;
an open is provided at the top of the board to connect the chamber and the connect-in space; and
a passageway with a blocker is provided between the connect-in space and the mist blow-off channel.

2. The nebulizer according to claim 1, wherein the peristaltic pump with rollers contains an elastic tube connected with the steel needle.

3. The nebulizer according to claim 2, wherein the nebulizer further comprises:
a bottle, with essential oil, connected with the module;
a liquid suction tube immersed into the bottle for sucking and supplying fluid to the steel needle by the peristaltic pump with rollers.

4. The nebulizer according to claim 1, wherein the nebulizer further comprises:
a control board connecting to control the peristaltic pump with rollers and the needle nebulizer.

5. The nebulizer according to claim 4, wherein the control board contains a PCB board with micro control units, plug-in interfaces and operating buttons, the PCB board controls the peristaltic pump with rollers and the needle nebulizer.

6. The nebulizer according to claim 1, wherein the connect-in space and the mist blow-off channel of the needle nebulizer are designed parallelly.

7. The nebulizer according to claim 1, wherein the needle nebulizer further comprises a fan, and the fan is mounted on the module, with an intake from a direction of the steel plate, and blows the air into the inlet of the chamber.

8. The nebulizer according to claim 1, wherein the needle nebulizer further comprises a socket, the steel needle comprises a rear end, and the rear end of the steel needle is held by the socket which is mounted to the module.

* * * * *